US009456876B2

(12) United States Patent
Hagn

(10) Patent No.: US 9,456,876 B2
(45) Date of Patent: Oct. 4, 2016

(54) DEVICE FOR CONNECTING CONVENTIONAL OR LAPAROSCOPIC INSTRUMENTS TO A ROBOT

(75) Inventor: Ulrich Hagn, Pähl (DE)

(73) Assignee: Deutsches Zentrum für Luft-und Raumfahrt e. V., Bonn (DE)

( * ) Notice: Subject to any disclaimer, the term of this patent is extended or adjusted under 35 U.S.C. 154(b) by 1905 days.

(21) Appl. No.: 11/270,987

(22) Filed: Nov. 12, 2005

(65) Prior Publication Data

US 2006/0195070 A1    Aug. 31, 2006

(30) Foreign Application Priority Data

Nov. 12, 2004    (DE) .................... 10 2004 054 866

(51) Int. Cl.
*A61B 19/00* (2006.01)
*A61B 17/34* (2006.01)
*A61B 17/00* (2006.01)

(52) U.S. Cl.
CPC ............ *A61B 34/70* (2016.02); *A61B 17/3421* (2013.01); *A61B 34/30* (2016.02); *A61B 2017/00482* (2013.01)

(58) Field of Classification Search
CPC .............. A61B 19/2203; A61B 19/22; A61B 2017/00477
USPC .......................... 606/130; 901/29; 74/490.06
See application file for complete search history.

(56) References Cited

U.S. PATENT DOCUMENTS

| 5,078,140 A * | 1/1992 | Kwoh ............................ 600/417 |
| 6,331,181 B1 * | 12/2001 | Tierney et al. ............... 606/130 |
| 7,166,114 B2 * | 1/2007 | Moctezuma De La Barrera et al. ............................. 606/130 |
| 2003/0195664 A1 | 10/2003 | Nowlin et al. |

FOREIGN PATENT DOCUMENTS

| WO | WO99/01261 | 1/1999 |
| WO | WO2004/014244 A2 | 2/2004 |

* cited by examiner

*Primary Examiner* — Diane Yabut
(74) *Attorney, Agent, or Firm* — Collard & Roe, P.C.

(57) ABSTRACT

To connect conventional or laparoscopic instruments to a robot that can be used for medical applications, there can be a device that has a first and a second circular cylinder segment having a continuous center bore is connected with the angled first segment affixed to the free end of a robot arm. This connection can be by way of an articulated joint that can be rotated by 180°. On one end surface of the second segment, there can be a third segment in the form of a flange, having a bore that is coaxial with the continuous center bore in the second segment. There is also a rolling joint which can be used to allow the device to rotate. Around the bore of the flange, there can be supply technology and data technology connection elements and a locking mechanism for coupling end effectors on and off.

11 Claims, 4 Drawing Sheets

DEVICE FOR CONNECTING CONVENTIONAL OR LAPAROSCOPIC INSTRUMENTS TO A ROBOT

CROSS REFERENCE TO RELATED APPLICATIONS

Applicants claim priority under 35 U.S.C. §119 of GERMAN Application No. DE 10 2004 054 866.8, filed on Nov. 12, 2004, the disclosure of which is hereby incorporated herein by reference.

BACKGROUND OF THE INVENTION

1. Field of the Invention

The invention relates to a device for connecting conventional or laparoscopic instruments to an arm of a robot that can be used for medical applications.

Highly specialized robots are used in medical applications. Such robots generally carry either conventional instruments or laparoscopic instruments, whereby the instruments of the second group generally have a rod-shaped shape, which makes it possible for laparoscopic instruments to be introduced into the body of a patient through small openings. With laparoscopic instruments, the rod-shaped part of such an instrument is partially or mainly located in the body of the patient during an intervention. For safety reasons, removal of the instrument from the body of the patient is possible, through the small opening, only along the axis of the rod-shaped part, axis of the instrument runs coaxial to the robot axis, and if it coincides with the latter, the robot axle can be configured as a hollow shaft unit, so that the instrument can be removed in conformity therewith.

At the present time, only a robot sold by the company Computer Motion, under the designation "Roboter: Aesop" is known, to which laparoscopic instruments can be connected.

However, the current state of the art ignores the need for connecting both laparoscopic and conventional instruments, since the two groups of instruments have been assigned to different robot markets within medical robotics. Furthermore, an electrical connection of the instruments to be guided to the robot arm has not been present in the prior art.

SUMMARY OF THE INVENTION

It is therefore the task of the invention to reconfigure a robot that can be used for medical applications, i.e. its last member, so that both conventional and laparoscopic instruments can be connected.

According to the invention, this task is accomplished, via a device for mechanically and electrically connecting conventional or laparoscopic instruments to an arm of a robot that can be used for medical applications.

The device can include a second circular cylinder segment having a continuous center bore which is connected with an angled first segment affixed to the free end of the robot arm, by way of an articulated joint that can be rotated by approximately 180°. In addition, with the end surface of the second segment, there can be a third segment in the form of a flange, having a bore that is coaxial with the continuous center bore in the second segment. The second segment can have supply technology and data technology connection elements. In addition, this device can have a locking mechanism for coupling end effectors on and off, and which can be provided, by way of a rolling joint.

The robot joint that has been reconfigured according to the invention thereby permits both mechanical and electrical connection of such rod-shaped laparoscopic instruments, as well as conventional instruments. Therefore, the device according to the invention creates a robot that can be universally used for medical applications.

BRIEF DESCRIPTION OF DRAWINGS

Other benefits and features of the present invention will become apparent from the following detailed description considered in connection with the accompanying drawings. It is to be understood, however, that the drawings are designed as an illustration only and not as a definition of the limits of the invention.

In the drawings, wherein similar reference characters denote similar elements throughout the several views.

DETAILED DESCRIPTION OF THE DRAWINGS

Figure 1:
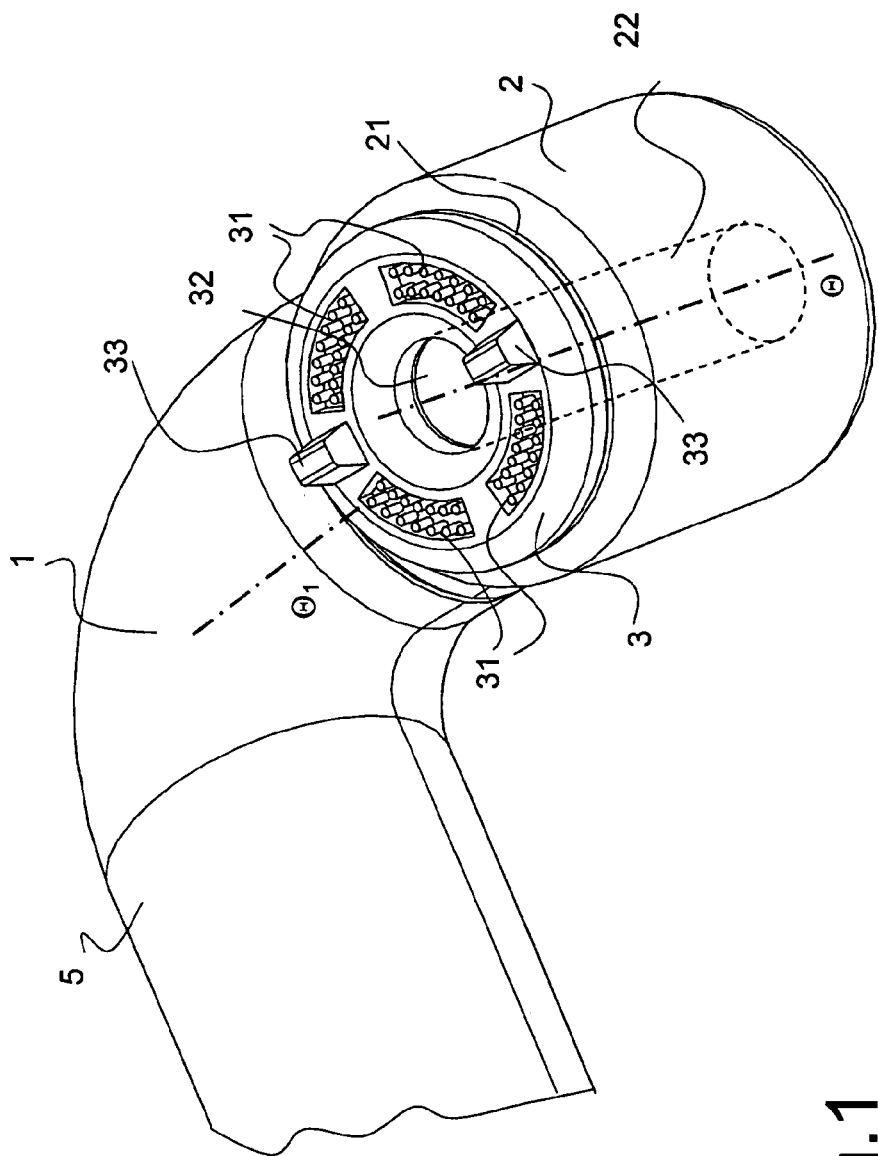
FIG. 1 is a schematic representation of a reconfigured robot flange.

Referring now in detail to the drawings and, in particular, FIG. 1 shows a configuration of the last axle of a robot, particularly one that can be used for medical applications. For both laparoscopic and non-laparoscopic, i.e. conventional instruments to be connected to a robot for medical applications, there can be an angled first segment 1 which is affixed to the free end of a robot arm 5 at a first end. First segment can be connected at a second end to a circular cylindrical segment 2, by way of an articulated joint $\Theta$.

A third segment, in the form of a robot flange 3, is attached to an end surface 21 of second segment 2, by way of rolling joint $\Theta$. Rolling joint $\Theta$ has a bore 32, which is continued coaxial to a continuous center bore 22 in second segment 2.

Second segment 2 can include supply technology and data technology connection elements in the form of data connection elements such as pins 31 for the instruments. Second segment 2 can also include a locking mechanism 33 that is configured on robot flange 3, around bore 32, as indicated schematically. These locking mechanisms 33 can be used to couple end effectors on and off.

The locking mechanism can, in addition, also be configured so as to be electronically controllable. Furthermore, locking mechanism 33 is designed so that it can also serve as mechanical protection against incorrect assembly of end effectors to be connected.

Laparoscopic instruments for robot-assisted minimally invasive surgery are generally relatively long and rod-shaped. Miniaturized effectors/sensors are situated at one end, the distal end of laparoscopic instruments. These sensors can be in the form of a pliers bit, scissors, a CCD camera, and the like, while the components necessary for operation of the effectors are disposed at the other end, the proximal end of such instruments.

Since the proximal end of such an instrument remains outside of the patient's body, it generally has a clearly greater construction volume. As already explained initially, it must be possible, for safety reasons, among other things, to remove laparoscopic instruments for robot-assisted minimally invasive surgery from the body of a patient along their longitudinal axis, at any time, without having to move the patient and/or the robot.

Figure 2:
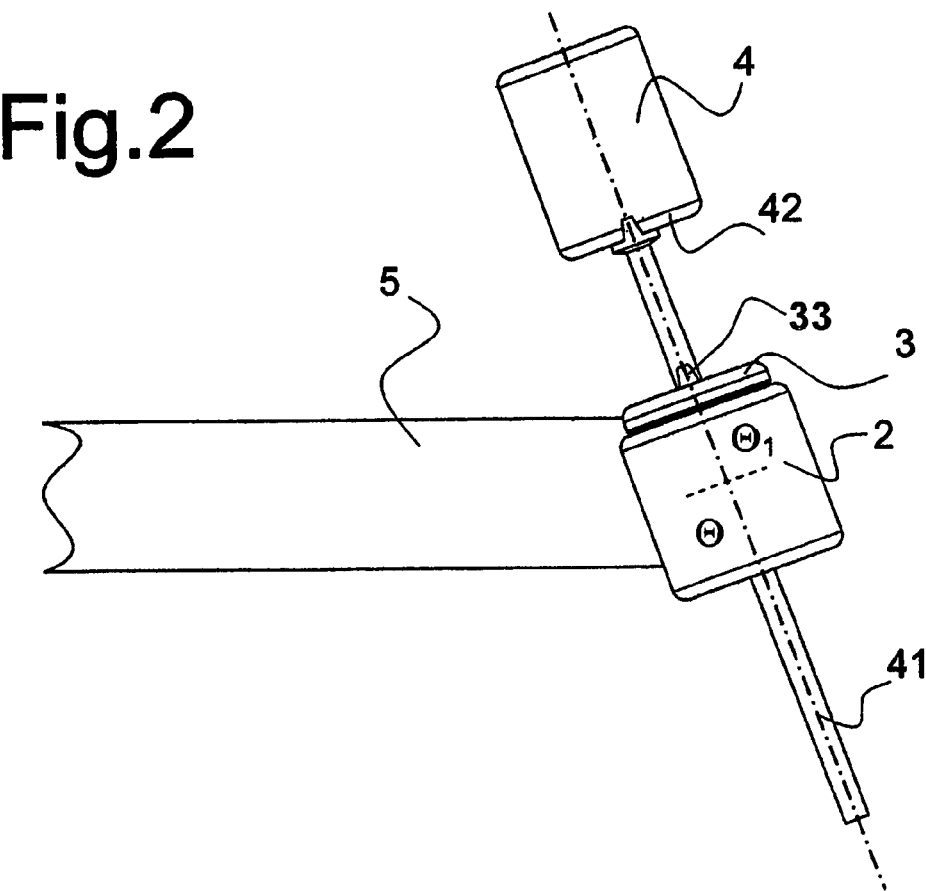
FIG. 2 is a schematic representation of a laparoscopic instrument that can be connected with the robot flange.
Figure 3:
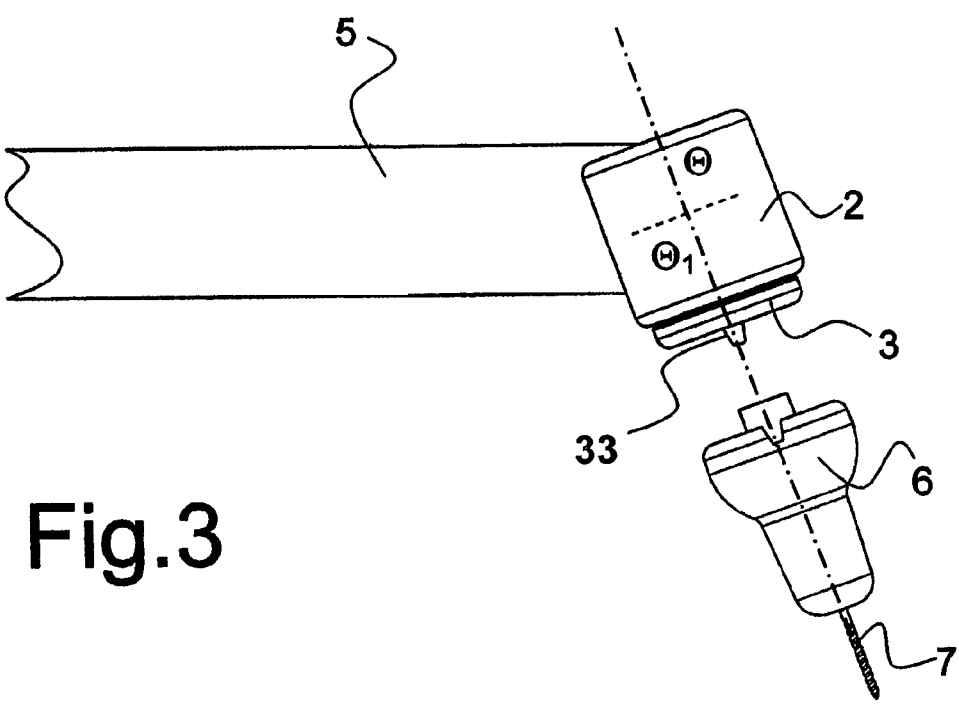
FIG. 3 is a schematic representation of a conventional instrument that can be connected with the robot flange.

FIG. 2 shows the assembly of a laparoscopic instrument 4, which is inserted through joint Θ with its rod-shaped shaft 41. Connection of laparoscopic instrument 4 occurs via a counter-piece on underside 42 of instrument 4, which is adequate for the supply and data connection elements 31 as well as locking mechanism 33, not shown in greater detail in FIG. 2.

To connect a non-laparoscopic conventional instrument 6 with a drill 7 that is inserted into it, for example, the privileged direction of joint $\Theta_1$ is rotated by 180°. Conventional instrument 6 is flanged onto the end surface face of second segment 2, and thereby is not inserted through the joint Θ.

Figure 4:
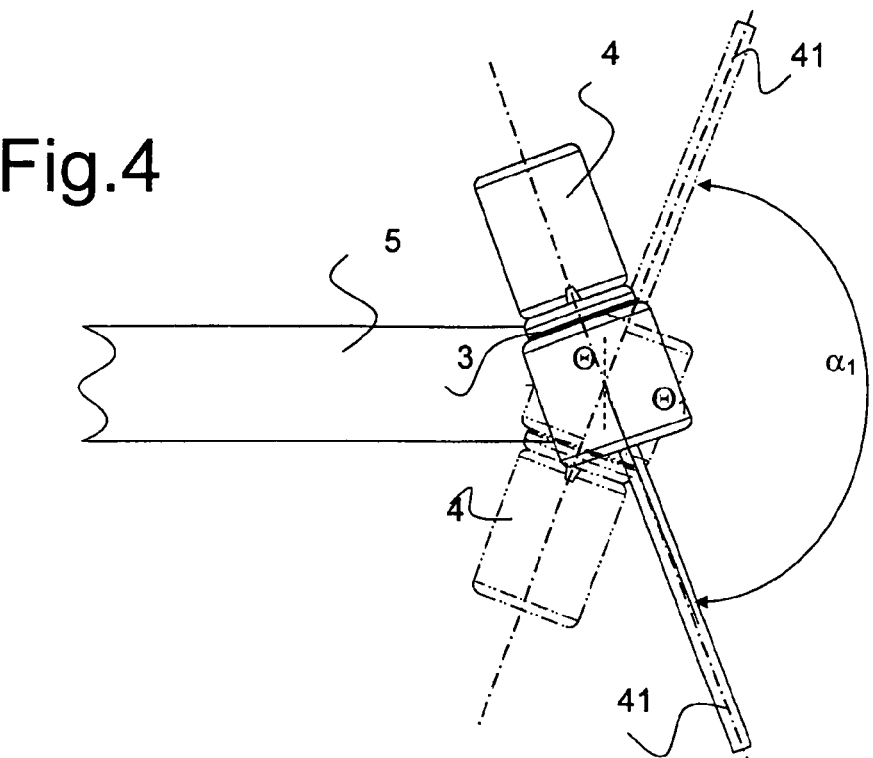
FIG. 4 is a schematic representation of the joint angle range for laparoscopic and/or conventional instruments.
Figure 5:
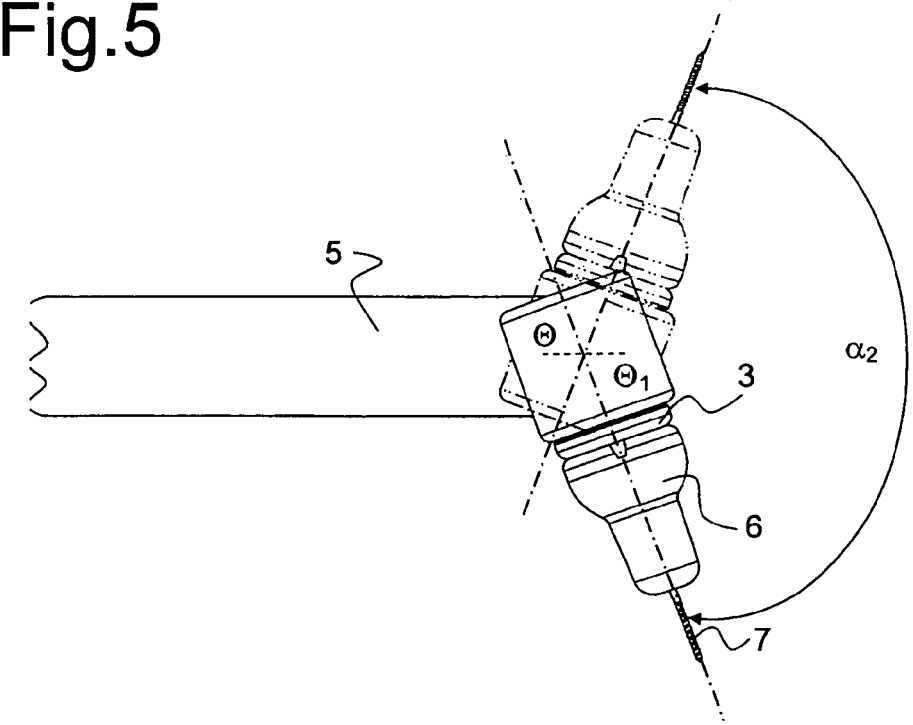
FIG. 5 is a schematic representation of the joint angle range for laparoscopic and/or conventional instruments.

As shown in FIGS. 4 and 5, a movement along angle α1 is possible from using laparoscopic instruments 4, with articulated joint $\Theta_1$. In addition, a movement along angle α2 is possible using conventional instrument 6. The required joint angle range for articulated joint $\Theta_1$ is therefore 180° plus $\alpha_{max}$ (where $\alpha_{max}$=max {α1, α2}).

Figure 6:
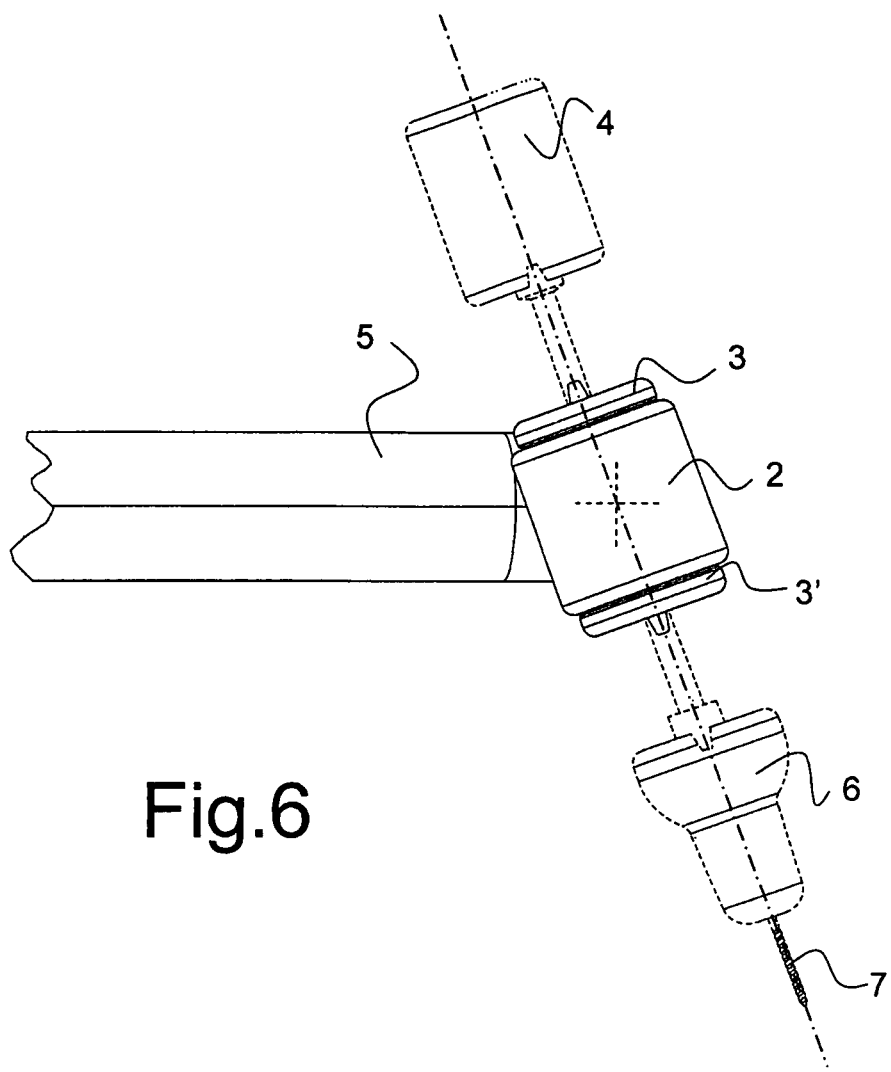
FIG. 6 a schematic representation of a connection possibility for the two instrument types.

If the angles α1 are supposed to be enlarged, a variant of the configuration described above is shown in FIG. 6, wherein two flanges 3 and 3' are disposed on second segment 2. With the embodiment according to FIG. 6, the configuration angle of approximately 180 degrees is eliminated, since both instrument types can be flanged on without reconfiguring joint $\Theta_1$. FIG. 6 schematically indicates the possibility of connecting either a laparoscopic instrument 4 or, instead, a conventional non-laparoscopic instrument 6.

Accordingly, while only at least one embodiment of the present invention have been shown and described, it is obvious that many changes and modifications may be made thereunto without departing from the spirit and scope of the invention.

REFERENCE SYMBOL LIST 1 first segment
2 second segment
21 end surface
22 center bore
3, 3' third segment/flange
31 connection possibilities
32 coaxial bore
33 locking mechanism
5 robot arm
Θ rolling joint
$\Theta_1$ articulated joint

What is claimed:

1. A device for connecting instruments to an arm of a robot that can be used for medical applications comprising:
   a) an angled first segment mountable to a free end of a robot arm;
   b) a circular cylindrical segment having a continuous center bore and coupled to said angled first segment;
   c) an articulating joint $\theta_1$ that can be rotated, and which is coupled to said circular cylindrical segment;
   d) a flange forming a third segment, coupled to said circular cylindrical segment, said flange having a bore that is coaxial and continuous with said center bore in said circular cylindrical segment;
   e) a plurality of data technology connection elements for electrically connecting the circular cylindrical segment with a medical instrument coupled to said circular cylindrical segment;
   wherein said plurality of data technology connection elements are disposed around said bore of said flange;
   wherein said flange is disposed on an end of said circular cylindrical segment;
   f) said flange being provided with a locking mechanism for establishing a mechanical connection to medical instruments; and said flange being provided with the plurality of data technology connection elements; and
   said locking mechanism is designed so that it can also serve as mechanical protection against incorrect assembly of said medical instruments to be connected; and
   g) a rolling joint coupled to said circular cylindrical segment; and
   wherein said rolling joint is for coupling said circular cylindrical segment to said flange, and wherein said rolling joint is adapted so that a laparoscopic instrument can be inserted with its rod-shaped shaft through said rolling joint; and
   h) said circular cylindrical segment (2) can be rotated by 180° around said articulating joint $\theta_1$, so that the laparoscopic instrument (4) can be connected or a non-laparoscopic instrument (6) can be connected.

2. The device as in claim 1, wherein the circular cylindrical segment is adapted to connect a laparoscopic instrument at a proximal end of the circular cylindrical segment.

3. The device as in claim 1, wherein the circular cylindrical segment is adapted to connect a non-laparoscopic instrument at a distal end of the circular cylindrical segment.

4. The device as in claim 1, wherein the data technology connection elements are pins.

5. The device as in claim 1, wherein said circular cylindrical segment (2) can be rotated by more than 180° around said articulating joint $\theta_1$, so that the laparoscopic instrument (4) can be connected or the non-laparoscopic instrument (6) can be connected.

6. A device for connecting instruments to an arm of a robot that can be used for medical applications comprising:
   a) an angled first segment mountable to a free end of a robot arm;
   b) a circular cylindrical segment having a continuous center bore and coupled to said angled first segment;
   c) an articulating joint $\theta_1$ that can be rotated, and which is coupled to said circular cylindrical segment;
   d) a flange forming a third segment, coupled to said circular cylindrical segment, said flange having a bore that is coaxial and continuous with said center bore in said circular cylindrical segment;
   e) a plurality of data technology connection elements for electrically connecting the circular cylindrical segment with a medical instrument coupled to said circular cylindrical segment;
   wherein said plurality of data technology connection elements are disposed around said bore of said flange;
   wherein said flange is disposed on an end of said circular cylindrical segment;
   f) said flange being provided with a locking mechanism for establishing a mechanical connection to medical instruments; and said flange being provided with the plurality of data technology connection elements; and
   g) a rolling joint coupled to said circular cylindrical segment; and wherein said plurality of data technology connection elements are disposed around said bore of said flange; and h) said circular cylindrical segment (2) can be rotated by 180° around said articulating joint $\theta_1$, so that a laparoscopic instrument (4) can be connected or a non-laparoscopic instrument (6) can be connected.

7. The device as in claim 6, wherein said rolling joint is for coupling said circular cylindrical segment to said flange.

8. The device as in claim 6, wherein the circular cylindrical segment is adapted to connect a laparoscopic instrument at a proximal end of the circular cylindrical segment.

9. The device as in claim 6, wherein the circular cylindrical segment is adapted to connect a non-laparoscopic instrument at a distal end of the circular cylindrical segment.

10. The device as in claim 6, wherein the data technology connection elements are pins.

11. The device as in claim 6, wherein said circular cylindrical segment (2) can be rotated by more than 180° around said articulating joint $\theta_1$, so that the laparoscopic instrument (4) can be connected or the non-laparoscopic instrument (6) can be connected.

* * * * *